United States Patent [19]

Heil

[11] 4,340,366
[45] Jul. 20, 1982

[54] WATER/AIR SPRAY SYSTEM FOR DENTAL HANDPIECE

[75] Inventor: Donald J. Heil, Lake Villa, Ill.

[73] Assignee: American Hospital Supply Corporation, Evanston, Ill.

[21] Appl. No.: 236,642

[22] Filed: Feb. 23, 1981

[51] Int. Cl.³ .............................................. A61C 1/12
[52] U.S. Cl. ..................................... 433/82; 239/318
[58] Field of Search ................. 433/82, 84, 85, 87, 433/126; 173/74; 239/318

[56] References Cited

U.S. PATENT DOCUMENTS

| | | | |
|---|---|---|---|
| 1,039,728 | 10/1912 | Gilmore | 433/87 |
| 2,855,672 | 10/1981 | Franwick et al. | 433/84 |
| 3,175,293 | 3/1965 | Borden | 433/127 |
| 3,256,604 | 6/1966 | Borden | 433/82 |
| 3,716,194 | 2/1973 | Miller | 239/318 |
| 3,952,416 | 4/1976 | Lingenhöle | 433/82 |

FOREIGN PATENT DOCUMENTS 626143  4/1963  France ................................. 433/82

Primary Examiner—Gene Mancene
Assistant Examiner—John J. Wilson
Attorney, Agent, or Firm—Tilton, Fallon, Lungmus

[57] ABSTRACT

A dental handpiece having an improved water/air spray system including a pair of substantially parallel tubes, one for water and the other for chip air, extending through the handle of the handpiece and terminating in a nozzle chamber having a discharge orifice. The tubes are generally cylindrical but are partially deformed at their distal ends, such deformation constituting a flattening of adjacent wall portions of the respective tubes. Such adjacent wall portions are disposed in contiguous relation and are cut away for a limited distance at the discharge end of the tube assembly to define the unitary nozzle chamber. The wall of the chamber is provided with a water-deflecting surface aligned with the water passage and sloping inwardly and distally toward the orifice to deflect water from the water passage into the path of air discharged from the chip air passage immediately prior to the discharge of said water/air spray from the nozzle chamber.

4 Claims, 11 Drawing Figures

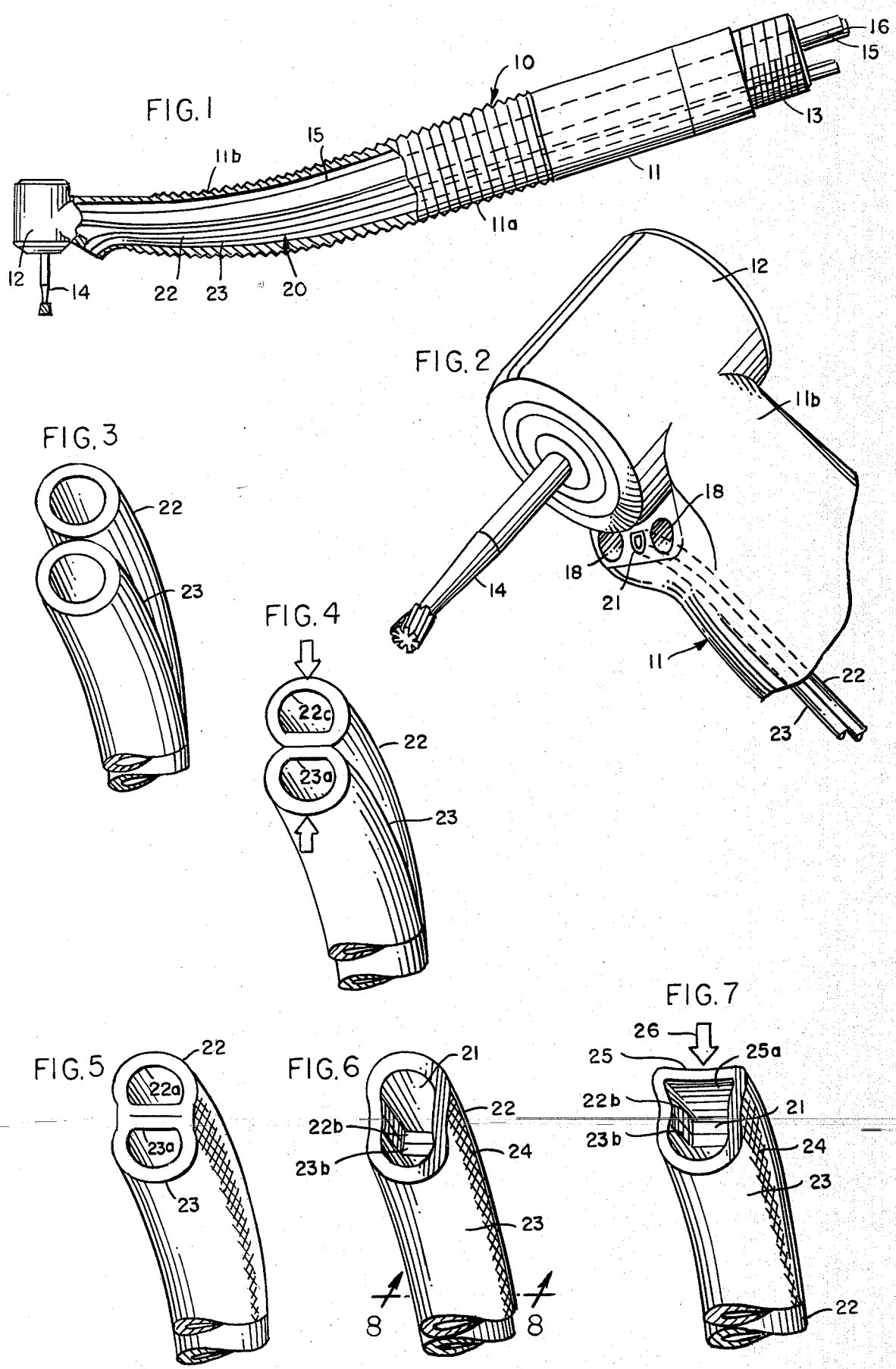

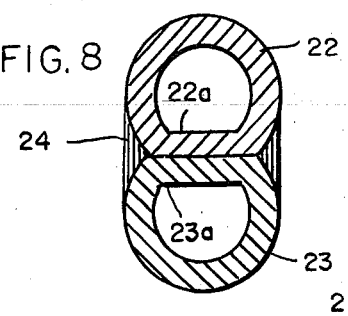
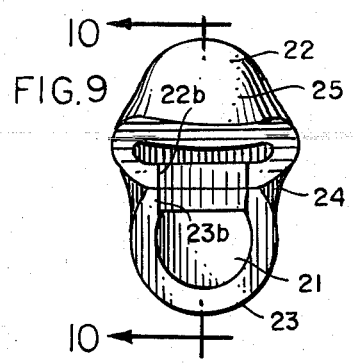
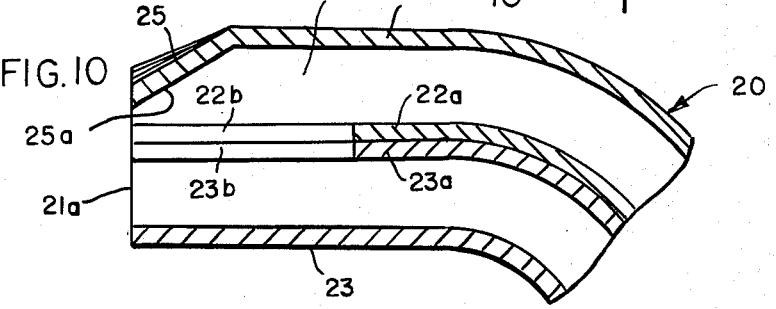
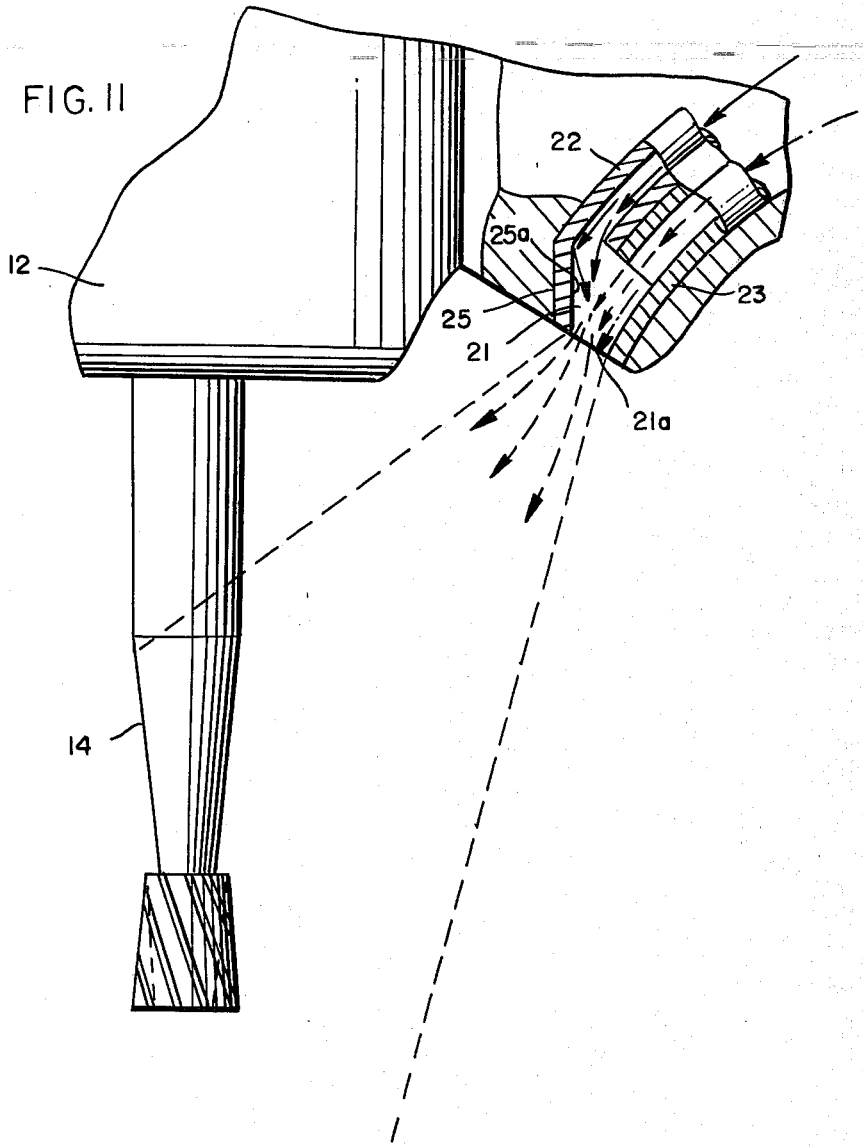

WATER/AIR SPRAY SYSTEM FOR DENTAL HANDPIECE

BACKGROUND

High speed dental handpieces are commonly provided with nozzles for directing air and water in spray form towards the tips of dental burs. The water/air spray performs the dual functions of cooling the work area and clearing debris from that area. Intermixing of water and air to form the aerosol spray may occur either internally or externally of the handpiece. Patent 3,952,416 shows an internal mixing system in which a portion of the drive air is diverted and mixed with water in a chamber within the neck of the handpiece, the mixture then being discharged through a passage in the head of that handpiece. Other patents disclosing remote or internal mixing are U.S. Pat. Nos. 3,256,603 and 3,175,293. External mixing is typically provided, at least in one commercial line of handpieces, by concentric water and chip air tubes which have their discharge ends disposed immediately adjacent the heads of such handpieces. Simultaneous discharge of air and water from the pressurized line causes an aerosol spray to be directed towards the dental bur driven by such a handpiece. Other patents indicating the state of the art are U.S. Pat. Nos. 2,855,672, 2,369,880, 3,061,930, 3,815,241, 1,039,728, 3,199,196, and 1,270,736 (Ger. Pat. No.).

Co-pending co-owned application Ser. No. 109,761, filed Jan. 7, 1980, discloses a high speed dental handpiece having a single nozzle chamber receiving water and air (either chip air or drive air) from lines which extend through the handle of the handpiece. The chamber and its outlet are oval in cross sectional configuration with the long axis of the oval lying in the same plane as the rotational axis of the bur and with the nozzle opening being directed towards the tip of a mounted bur of standard length. Consequently, the oval spray pattern, elongated in a direction along the bur axis but confined in directions lateral to that axis, provides effective cooling and clearing actions for burs of shorter and longer shank length, as well as for burs of standard shank length, without the undesirable discharge of excessive volumes of water. In addition, the nozzle chamber serves as a pre-convergence chamber which effectively increases the distance between the separate outlets of the water and chip air tubes and the bur, and thereby insures proper air/water intermixing even for handpieces of smaller or miniature dimensions.

The air and water tubes leading to the nozzle chamber extend through the handle of the handpiece in generally parallel side-by-side relation. The nozzle chamber is formed by removing or cutting away contiguous wall portions from such tubes at the extreme distal ends thereof. Although such tubes are cylindrical for the most part, the contiguous wall portions approaching the discharge end of the tube assembly are flattened and such tubes are secured together with such flattened wall portions in direct contact with each other. The result is that the nozzle chamber, formed by removal of such flattened contiguous wall portions at the distal end of the spray tube assembly, is generally oval in cross sectional configuration.

While such construction has in general been found highly effective, circumstances may exist which would tend to reduce the effectiveness of the interaction between water and air in the nozzle chamber and thereby reduce the completeness of aerosolization. Should the pressure of air for spray development be relatively low, as might possibly occur when such air is bled from the drive air passage at a point adjacent the proximal end of the handpiece, the aerosol spray may include undesirably large water droplets and, if the air flow should be reduced even further, the discharge of water in spray form may become erratic.

Accordingly, it is an object of this invention to modify the structure disclosed in the aforementioned co-pending application to achieve greater aerosolization at lower air pressures. It has been found that such an objective may be attained by deforming the wall of the pre-mixing or pre-convergence chamber so that water entering that chamber is deflected into the path of air entering the same chamber. Such a construction insures that the water and air streams converge sufficiently at, or immediately upstream from, the discharge orifice to produce a high degree of aerosolization even at relatively low air pressures. The deflecting surface may be easily and effectively formed in a final stage of manufacturing the spray tube assembly by bending a distal wall portion of the nozzle chamber—specifically, a portion provided by the water tube that is located diametrically opposite from the cutout portion of that tube—so that such wall portion slopes inwardly and distally to the discharge orifice. Water impinging on the sloping surface will therefore be deflected into the mainstream of air entering the nozzle chamber from the air passage, promoting more complete aerosol development than might otherwise be achieved under low air pressure conditions.

Other objects, features, and advantages of the invention will become apparent from the drawings and specification.

DRAWINGS

FIG. 1 is a side elevational view, partly in section, of a dental handpiece embodying this invention.

FIG. 2 is a perspective view of the head and neck portions of such a handpiece.

FIGS. 3–7 are a series of fragmentary perspective views illustrating the sequence of steps in the construction of the spray tube assembly of the fluid discharge end thereof.

FIG. 8 is a cross sectional view taken along line 8—8 of FIG. 6.

FIG. 9 is an end view of the distal end of the spray tube assembly.

FIG. 10 is a longitudinal sectional view taken along line 10—10 of FIG. 9.

FIG. 11 is a fragmentary side elevational view, partly in section, showing the structural relationship and functioning of the spray tube assembly and its discharge chamber.

DETAILED DESCRIPTION

Referring to the drawings, the numeral 10 generally designates a contra-angle turbine-driven dental handpiece having an elongated hollow handle 11 terminating at its distal end in a head assembly 12 and at its proximal end in an end plug or connector 13. The plug is externally threaded so that the handpiece's proximal end may be coupled to a conventional hose leading to any of a variety of dental units or consoles which provide the pressurized sources of supply for air and water for handpiece operation. As shown, the main body portion 11*a* of the handle is straight and tapers gradually in a distal direction towards the angularly-oriented neck portion 11*b* leading to head assembly 12. An air-driven turbine (not shown) is mounted within the head assembly and includes a chuck for releasably supporting a conventional dental bur 14. A drive air tube 15 extends through the handle to supply air under pressure for driving the turbine. Exhaust air is discharged from the turbine into the hollow handle and passes from the handle into the hose (not shown) through a tubular extension 16 of plug 13. The drive air and exhaust air extensions 15 and 16, respectively, provide connections for direct communication to the drive air and exhaust air conduits of the hose (not shown).

If desired, a light-transmitting waveguide, typically in the form of a sheathed glass fiber bundle, may extend through the handpiece handle for illuminating the work area. Although such a waveguide forms no direct part of this invention, it does demonstrate that space within the handle of the handpiece is at a premium because of the various conduits and elements that must be passed through it, and in the further fact that there is only limited available space for the spray tube assembly 20 and its nozzle chamber 21 to be described in detail hereinafter. FIG. 2 reveals that where fiber optic illumination is provided, the light bundle may be bifurcated near the head of the handpiece to provide a pair of spaced light-emitting end surfaces 18. Such arrangement is helpful in reducing shadows in the work area at the tip of bur 14 but it also restricts the available space for fluid discharge chamber 21, especially where the handpiece is of the miniaturized type as shown.

The spray tube assembly 20 consists primarily of a pair of small-bore tubes 22 and 23 which extend through plug 13 and through handle 11 to a discharge point adjacent head assembly 12. Tubes 22 and 23 are water and chip air tubes, respectively, for delivering water and air to produce a cooling and debris-clearing aerosol spray at the head end of the handpiece (FIG. 11). The term "chip air" is used to indicate that in the preferred operation of the handpiece tube 23 would normally carry air at pressures of approximately 60 psi, well above the pressure of drive air (typically about 30 psi) carried by drive air tube 15. Depending on the controls used and the dental unit to which handpiece 10 is connected, chip air tube 23 may be used separately to discharge a jet of dry air for dislodging chips or cutting debris from the work area. For purposes of this invention, such independent use of tube 23 bears no particular significance; however, to help in distinguishing tube 23 from other air transmitting tubes, and because even when used in conjunction with water tube 22 to produce an aerosol spray the chip air tube 23 does indeed function to remove cutting debris from the work area, the term "chip air" will be used extensively herein in referring to tube 23.

At the distal end of the handpiece, the two tubes 22 and 23 are secured together by solder, welding, or other suitable adhesive or bonding agent. Preferably, the attachment commences along that section of the tube assembly which extends through the neck portion 11*b* of the handle and continues distally to the ends of the tubes.

Throughout most of their length, tubes 22 and 23 are cylindrical in configuration. However, as they approach the head end of the handpiece, the adjacent wall portions 22*a* and 23*a* are flattened as depicted in FIG. 8. The planar opposing wall portions 22*a* and 23*a* are disposed in contiguous relation and are fixed in that relation by solder (or other bonding agent) 24. The result is that the passages of the respective tubes are reduced slightly in cross section in the area of deformation and interconnection; however, such deformation also substantially reduces the combined outside dimensions of the two tubes when measured along a line passing through the axes of both.

FIGS. 3–7 represent in somewhat schematic fashion the succession of steps for fabricating the nozzle end of the spray tube assembly. The two tubes 22 and 23 are first arranged with their distal ends in juxtaposition as shown in FIG. 3. Compressive force is then applied to reduce the combined cross sectional dimension of the paired tubes and to deform the contacting walls 22*a* and 23*a* so that they assume the planar configurations depicted in FIG. 4. The deformed tubes are then fixed together in their positions of mutal engagement by suitable bonding means represented in FIGS. 5–7 by solder 24. Thereafter, the common wall portions which separate the passages of the respective tubes at the distal end of the assembly are cut away to 22*b* and 23*b* to define the oval-shaped nozzle chamber (FIG. 6).

Referring to FIG. 10, it will be noted that although chamber 21 is of generally oval cross section along much of its length, a wall portion 25 of water spray tube 22 is reformed so that it slopes inwardly and distally to discharge orifice 21*a* of the nozzle chamber 21. Specifically, the reformed or deformed wall portion 25 is located at the distal end of water tube 22 in an area diametrically disposed with respect to cutout 22*b*. The inwardly and distally sloping inner surface 25*a* of wall portion 25 thus provides a deflecting surface for directing water towards that portion of the nozzle chamber 21 that is in direct alignment with the passage of air tube 23.

FIG. 7 depicts a final step in the fabrication of the spray tube assembly wherein force is applied in the direction of arrow 26 to bend wall portion 25 downwardly and thereby form the inwardly and forwardly (distally) inclined deflecting surface 25*a* at the extreme distal end of nozzle chamber 21.

After the spray tube assembly 20 has been mounted within the hollow handle of the handpiece, the parts assume the orientation most clearly illustrated in FIG. 11. The nozzle chamber 21 has its discharge orifice 21*a* facing the work area at the cutting end of bur 14. Water tube 22 is disposed above air tube 23, and reformed wall portion 25 has its outer surface facing in the direction of head 12. The result is that cooling and chip-clearing air/water spray will be properly directed towards the work area, and towards the tip of dental bur 14, when the system is in use.

Water enters nozzle chamber 21 as indicated by solid arrows in FIG. 11. At least some of the water impinges on the sloping surface 25*a* of wall portion 25 and is deflected into the path of air streaming from air tube 23 into the nozzle chamber. Although it is apparent that some water will not directly contact deflecting surface 25*a*, its flow will nevertheless be diverted so that it enters that portion of the nozzle chamber in general alignment with air tube 23. Proper air/water mixing, and effective aerosolization, are therefore assured even at relatively low chip air pressures, that is, at pressures of 25 psig or less. Even at higher pressures of 40 psig or more, it is believed that the provision of deflector 25 promotes more complete aerosolization.

The depth or axial dimension of chamber 21 will vary depending on the cross sectional dimensions of the passages defined by tubes 22 and 23 and by other factors such as the fluid pressures involved. In a system in which the inside diameters of such tubes adjacent the head of the handpiece are approximately 0.02 inches, resulting in a nozzle chamber having an oval cross sectional configuration (at its proximal end) measuring approximately $0.02 \times 0.04$ inches in its transverse dimensions, a chamber depth or axial dimension of approximately 0.06 inches has been found effective. In general, the depth or axial dimension of chamber 21 must not be so great that the back pressure created by the chamber exceeds the supply pressure of either the water or the air delivered by tubes 22 and 23, respectively. Wall portion 25 obviously constricts chamber 21 when the distal end of the tube assembly is viewed in vertical section (FIGS. 10 and 11); the extent of such constriction should not be more than necessary to deflect the flow of water and insure complete aerosolization. In general, the vertical dimension of the discharge orifice 21*a* should be substantially greater than the undeformed inside diameter of either of the tubes 22 or 23. Stated differently, the distal end of deflector wall portion 25 should not extend to the plane of flattened wall portion 22*b* of water tube 22.

While in the foregoing I have disclosed an embodiment of the invention in considerable detail for purposes of illustration, it will be understood by those skilled in the art that many of these details may be varied without departing from the spirit and scope of the invention.

I claim:

1. A dental handpiece comprising a hollow handle having a proximal end portion adapted for connection to a supply hose containing conduits for the supply of air and water to said handle, an elongated body portion, and a neck portion terminating at its distal end in a head assembly; said head assembly including a housing, an air turbine within said housing adapted to be driven by air supplied to said handle, and a chuck for operatively connecting a dental bur to said turbine; wherein the improvement comprises said handle containing a spray tube assembly comprising a pair of tubes defining passages for conducting water and air from the proximal end of said handpiece to a nozzle disposed adjacent said head assembly; said spray tube assembly including a distal section along which said tubes have adjacent wall portions joined together; said adjacent wall portions of said tubes being removed at said distal section to provide a cutout and to define a unitary nozzle chamber having a discharge orifice for directing a spray of water and chip air towards the cutting end of a dental bur; a portion of said water-conducting tube defining a wall portion of said nozzle chamber diametrically opposite from said cutout providing a deflecting surface aligned with the water passage and sloping inwardly and distally towards said orifice to deflect water from said water passage into the path of air discharged from said air passage and immediately prior to discharge of said spray from said orifice.

2. The handpiece of claim 1 in which each of said tubes is generally cylindrical in configuration and in which said adjacent wall portions are flattened and disposed in mutual engagement.

3. The handpiece of claim 1 in which said water and air tubes are symetrical in relation to a vertical midplane, the dimension of said orifice measured along said plane being substantially greater than the width of the passage of said air tube.

4. The handpiece of claim 3 in which said vertical plane extends along the rotational axis of said turbine, chuck, and bur.

* * * * *